(12) United States Patent
Kimoto et al.

(10) Patent No.: US 11,653,901 B2
(45) Date of Patent: May 23, 2023

(54) ULTRASOUND DIAGNOSTIC APPARATUS, RECORDING MEDIUM, AND CONSOLE GUIDE DISPLAY METHOD (71) Applicant: Konica Minolta, Inc., Tokyo (JP)

(72) Inventors: Takashi Kimoto, Yokohama (JP); Toshio Oka, Yokohama (JP)

(73) Assignee: KONICA MINOLTA, INC., Tokyo (JP)

( * ) Notice: Subject to any disclaimer, the term of this patent is extended or adjusted under 35 U.S.C. 154(b) by 148 days.

(21) Appl. No.: 16/744,377

(22) Filed: Jan. 16, 2020

(65) Prior Publication Data

US 2020/0261062 A1 Aug. 20, 2020

(30) Foreign Application Priority Data

Feb. 14, 2019 (JP) .............................. JP2019-024390

(51) Int. Cl.
*A61B 8/00* (2006.01)
(52) U.S. Cl.
CPC .............. *A61B 8/54* (2013.01); *A61B 8/463* (2013.01); *A61B 8/469* (2013.01)
(58) Field of Classification Search
CPC ........... A61B 8/54; A61B 8/469; A61B 8/463; A61B 8/465; A61B 8/4405; A61B 8/467; A61B 8/46
See application file for complete search history.

(56) References Cited

U.S. PATENT DOCUMENTS 11,241,216 B2 * 2/2022 Kurita ..................... G06F 3/14
2014/0164965 A1 * 6/2014 Lee .......................... A61B 8/467
715/765

(Continued)

FOREIGN PATENT DOCUMENTS

CN 107003404 A 8/2017
JP 2011-072532 A 4/2011
(Continued)

OTHER PUBLICATIONS

Office Action/Search Report issued in the related Chinese Application No. 202010086374.5 dated Nov. 3, 2022, with English translation.

(Continued)

*Primary Examiner* — Joseph M Santos Rodriguez
*Assistant Examiner* — Kaitlyn E Sebastian
(74) *Attorney, Agent, or Firm* — Lucas & Mercanti, LLP (57) ABSTRACT

There is provided an ultrasound diagnostic apparatus including: a first hardware processor that generates ultrasound image data based on a reception signal obtained through an ultrasound probe; a display; a second hardware processor that causes the display to display the generated ultrasound image data; and a console that has a plurality of physical operation devices that receive an operation input. The second hardware processor registers display position information, which is information regarding a display position within a display screen of a guide including an operation display component corresponding to each operation device of the console and information indicating a function set for the operation device, in a storage and displays the guide on the display based on the display position information stored in the storage.

17 Claims, 9 Drawing Sheets

(56) References Cited

U.S. PATENT DOCUMENTS

| | | | |
|---|---|---|---|
| 2016/0106394 A1* | 4/2016 | Kang | A61B 8/465 |
| | | | 600/437 |
| 2016/0132205 A1* | 5/2016 | Ramakrishnan | G06F 3/04817 |
| | | | 715/765 |
| 2016/0350503 A1* | 12/2016 | Jun | A61B 8/54 |
| 2018/0008232 A1* | 1/2018 | Mine | A61B 8/483 |
| 2018/0085097 A1* | 3/2018 | Kimoto | A61B 8/54 |
| 2020/0000430 A1* | 1/2020 | Chamberlain | A61B 8/4444 |

FOREIGN PATENT DOCUMENTS

| | | | |
|---|---|---|---|
| JP | 2015167648 A | 9/2015 | |
| JP | 2016-220830 A | 12/2016 | |
| JP | 2018-047080 A | 3/2018 | |

OTHER PUBLICATIONS

JPO, Office Action for the related Japanese Application No. 2019-024390, dated Jul. 12, 2022, with English translation.

* cited by examiner

ULTRASOUND DIAGNOSTIC APPARATUS, RECORDING MEDIUM, AND CONSOLE GUIDE DISPLAY METHOD

CROSS-REFERENCE TO RELATED APPLICATIONS

The entire disclosure of Japanese Patent Application No. 2019-024390 filed on Feb. 14, 2019 is incorporated herein by reference in its entirety.

BACKGROUND

Technological Field

The present invention relates to an ultrasound diagnostic apparatus, a recording medium, and a console guide display method.

Description of the Related Art

In ultrasound diagnosis, an examination can be performed repeatedly since the state of the heart or fetus is obtained as an ultrasound image with a simple operation of applying an ultrasound probe from the body surface or the inside of the body cavity and the safety is high. An ultrasound diagnostic apparatus used to perform such an ultrasound diagnosis is known. Ultrasound image data is obtained by transmitting ultrasound waves from the ultrasound probe to the subject, receiving reflected ultrasound waves by the ultrasound probe, and performing various processes on the received signal.

The console of the ultrasound diagnostic apparatus is generally complex due to a large number of operation devices, such as buttons. Accordingly, in order to recognize which function is assigned to which button, user skill is required. This is a burden on the user. Since the operation devices provided in the console are neither numbers nor content that can be easily memorized, it is common to attach a sticker, which indicates a function assigned to each operation device, to the console. However, since the assigned function may change depending on the image mode, state, and setting, it is difficult to cope with such a situation by attaching a sticker.

On the other hand, an ultrasound diagnostic apparatus is known which includes a main image monitor that displays an ultrasound image and a touch panel monitor that displays operation buttons for receiving a touch input in a fixed manner and in which functions of the operation buttons can be set on the touch panel monitor (refer to JP 2015-167648A).

SUMMARY

However, in the ultrasound diagnostic apparatus described in JP 2015-167648A, there is no mention of a configuration for the user to recognize the function assigned to each operation device provided in the console. For this reason, there is still a problem that the user has a burden in order to recognize the function assigned to each operation device provided in the console.

Even if a console guide (function display of each operation device of the console) is displayed, the guide is displayed so as to overlap the displayed operation button, which may make it difficult to operate and possibly interfere with ultrasound image diagnosis. In the case of an ultrasound diagnostic apparatus in which operation devices are displayed on a main image monitor that displays an ultrasound image, even if a console guide is displayed, the guide is displayed so as to overlap the ultrasound image. This may interfere with ultrasound image diagnosis. The console guide may be displayed at a location not intended by the user, and this may make it difficult to operate the console in ultrasound diagnosis.

It is an object of the present invention to easily operate a console without interfering with ultrasound image diagnosis.

To achieve at least one of the abovementioned objects, according to an aspect of the present invention, an ultrasound diagnostic apparatus reflecting one aspect of the present invention comprises: a first hardware processor that generates ultrasound image data based on a reception signal obtained through an ultrasound probe; a display; a second hardware processor that causes the display to display the generated ultrasound image data; and a console that has a plurality of physical operation devices that receive an operation input. The second hardware processor registers display position information, which is information regarding a display position within a display screen of a guide including an operation display component corresponding to each operation device of the console and information indicating a function set for the operation device, in a storage and displays the guide on the display based on the display position information stored in the storage.

To achieve at least one of the abovementioned objects, according to an aspect of the present invention, a non-transitory recording medium storing a computer readable program reflecting one aspect of the present invention causes a computer to function as: a first hardware processor that generates ultrasound image data based on a reception signal obtained through an ultrasound probe; a display; a second hardware processor that causes the display to display the generated ultrasound image data; and a console that has a plurality of physical operation devices that receive an operation input. The second hardware processor registers display position information, which is information regarding a display position within a display screen of a guide including an operation display component corresponding to each operation device of the console and information indicating a function set for the operation device, in a storage and displays the guide on the display based on the display position information stored in the storage.

To achieve at least one of the abovementioned objects, according to an aspect of the present invention, a console guide display method reflecting one aspect of the present invention comprises: generating ultrasound image data based on a reception signal obtained through an ultrasound probe; performing display control to display the generated ultrasound image data on a display; and registering display position information, which is information regarding a display position within a display screen of a guide including an operation display component corresponding to each operation device of a console having a plurality of physical operation devices that receive an operation input and information indicating a function set for the operation device, in a storage. In the display control, the guide is displayed on the display based on the display position information stored in the storage.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein.

DETAILED DESCRIPTION OF THE EMBODIMENTS

An embodiment of the present invention will be described in detail with reference to the accompanying diagrams. However, the scope of the invention is not limited to the disclosed embodiments.

Figure 1:
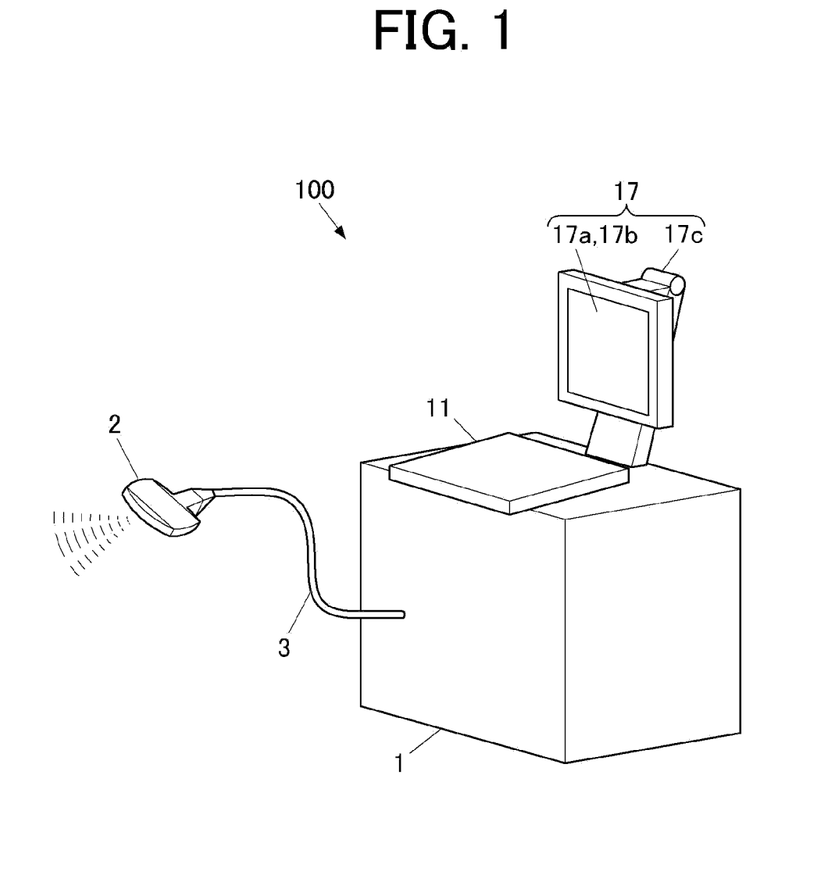
FIG. 1 is a diagram illustrating the appearance of an ultrasound diagnostic apparatus according to an embodiment of the present invention.

First, with reference to FIG. 1, the overall configuration of an ultrasound diagnostic apparatus 100 of the present embodiment will be described. FIG. 1 is a diagram illustrating the appearance of the ultrasound diagnostic apparatus 100 according to the present embodiment.

As illustrated in FIG. 1, the ultrasound diagnostic apparatus 100 includes an ultrasound diagnostic apparatus body 1 and an ultrasound probe 2. The ultrasound probe 2 transmits ultrasound waves (transmission ultrasound waves) to the inside of a subject such as a living body (not illustrated), and receives reflected waves of ultrasound waves (reflected ultrasound waves: echoes) reflected from the inside the subject. The ultrasound diagnostic apparatus body 1 is connected to the ultrasound probe 2 through a cable 3, and causes the ultrasound probe 2 to transmit transmission ultrasound waves to the subject by transmitting a driving signal as an electrical signal to the ultrasound probe 2 and images the internal state of the subject as ultrasound image data based on a received signal, which is an electrical signal generated by the ultrasound probe 2 in response to reflected ultrasound waves from the inside of the subject that are received by the ultrasound probe 2.

The ultrasound probe 2 includes a transducer 2a (refer to FIG. 2) that is a piezoelectric element. For example, a plurality of transducers 2a are arranged in a one-dimensional array in the azimuth direction (scanning direction). In the present embodiment, for example, the ultrasound probe 2 including 192 transducers 2a is used. The transducers 2a may be arranged in a two-dimensional array. The number of transducers 2a can be set arbitrarily. In the present embodiment, a convex electronic scan probe is used as the ultrasound probe 2 to perform an ultrasound scan by the convex scanning method. However, either a linear scanning method or a sector scanning method can also be adopted. Communication between the ultrasound diagnostic apparatus body 1 and the ultrasound probe 2 may be performed by wireless communication, such as ultra wide band (UWB) or the like, instead of wired communication through the cable 3.

A console 11 is a physical operation interface that is provided on the housing of the ultrasound diagnostic apparatus body 1 and receives operation inputs from users, such as doctors and engineers. A display operation interface 17 can be touched by the user and performs various displays. The display operation interface 17 includes a display 17a that performs display, a touch panel 17b that receives a touch operation input, and an arm 17c. The arm 17c is, for example, a biaxial arm provided in the housing of the ultrasound diagnostic apparatus body 1, and is a support that supports the display 17a (and the touch panel 17b) and allows the user to freely adjust the three-dimensional position of the display 17a. The arm 17c may be configured to be able to rotate the display 17a around the center of the display screen.

Figure 2:
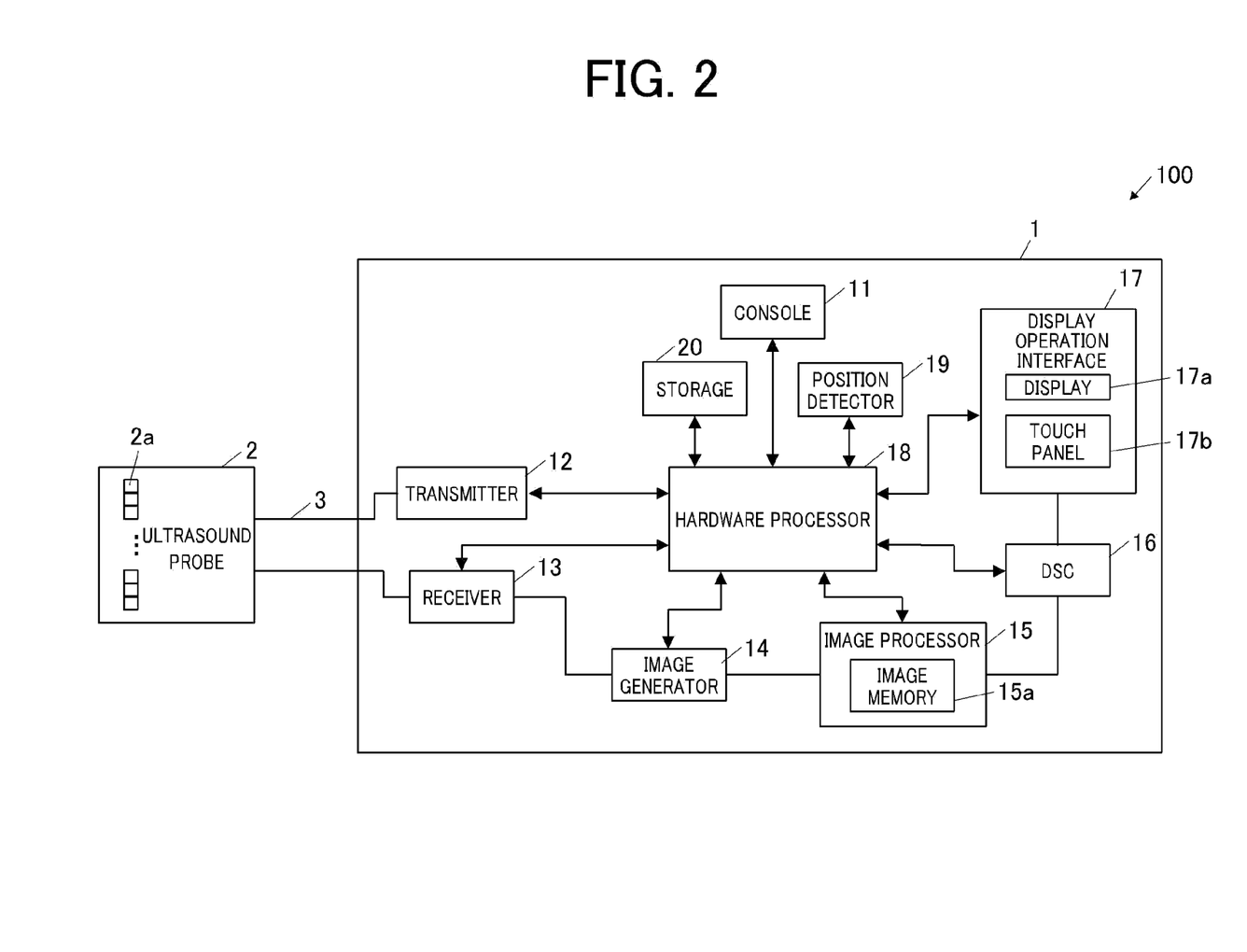
FIG. 2 is a block diagram illustrating the functional configuration of the ultrasound diagnostic apparatus.

Next, the functional configuration of the ultrasound diagnostic apparatus 100 will be described with reference to FIG. 2. FIG. 2 is a block diagram illustrating the functional configuration of the ultrasound diagnostic apparatus 100.

As illustrated in FIG. 2, the ultrasound diagnostic apparatus body 1 includes, for example, the console 11, a transmitter 12, a receiver 13, an image generator 14 (first hardware processor), an image processor 15, a digital scan converter (DSC) 16, the display operation interface 17, a hardware processor 18 (second hardware processor), a position detector 19, and a storage 20.

The console 11 includes, for example, various switches such as a rotary switch, buttons, a trackball, a mouse, a keyboard, and the like as physical operation devices for receiving an input of various image parameters and the like for displaying a command for giving an instruction to start diagnosis, data such as personal information of a subject, ultrasound image data, and the like on the display 17a, and outputs an operation signal of the input operation to the hardware processor 18.

The transmitter 12 is a circuit that supplies a driving signal, which is an electrical signal, to the ultrasound probe 2 through the cable 3 under the control of the hardware processor 18 so that transmission ultrasound waves are generated in the ultrasound probe 2. The transmitter 12 includes, for example, a clock generation circuit, a delay circuit, and a pulse generation circuit. The clock generation circuit is a circuit that generates a clock signal for determining the transmission timing or the transmission frequency of the driving signal. The delay circuit is a circuit that sets a delay time for each individual path corresponding to each transducer 2a and delays transmission of the driving signal by the set delay time so that focusing of the transmission beam configured by transmission ultrasound waves is performed. The pulse generation circuit is a circuit for generating a pulse signal as a driving signal at predetermined cycles. The transmitter 12 configured as described above drives, for example, consecutive some (for example, 64 transducers 2a) of the plurality of transducers 2a (for example, 192 transducers 2a) arranged in the ultrasound probe 2 to generate transmission ultrasound waves. Then, the transmitter 12 performs a scan by shifting the transducers 2a to be driven in the azimuth direction (scanning direction) each time transmission ultrasound waves are generated.

The receiver 13 is a circuit that receives a reception signal, which is an electrical signal, from the ultrasound probe 2 through the cable 3 under the control of the hardware processor 18. The receiver 13 includes, for example, an amplifier, an A/D conversion circuit, and a phasing addition circuit. The amplifier is a circuit for amplifying the reception signal at a preset gain for each individual path corresponding to each transducer 2a. The A/D conversion circuit is a circuit for analog-digital conversion (A/D conversion) of the amplified reception signal. The phasing addition circuit is a circuit that adjusts the time phase by giving a delay time to each individual path corresponding to each transducer 2a for the A/D converted reception signal and adds up the time phases (phasing addition) to generate sound ray data.

The image generator 14 performs envelope detection processing, logarithmic compression, and the like on the sound ray data from the receiver 13 and adjusts the dynamic range or the gain to perform brightness conversion under the control of the hardware processor 18, so that B (brightness) mode image data of pixels having brightness values as received energy can be generated. In other words, the B-mode image data expresses the strength of the reception signal by brightness. The image generator 14 may be able to generate ultrasound image data of other image modes, such as an A (amplitude) mode, an M (motion) mode, and image modes based on a Doppler method (pulse Doppler mode, color Doppler mode, and the like), in addition to B-mode image data as ultrasound image data in which the image mode is a B mode.

The image processor 15 performs image processing on the B-mode image data output from the image generator 14 in accordance with various set image parameters under the control of the hardware processor 18. The image processor 15 includes an image memory 15a that is a semiconductor memory, such as a dynamic random access memory (DRAM). The image processor 15 stores the B-mode image data subjected to the image processing in the image memory 15a in units of frames under the control of the hardware processor 18. The image data in units of frames may be referred to as ultrasound image data or frame image data. The image processor 15 sequentially outputs the image data generated as described above to the DSC 16 under the control of the hardware processor 18.

The DSC 16 converts the image data received from the image processor 15 into a display image signal under the control of the hardware processor 18, and outputs the display image signal to the display operation interface 17.

Display devices, such as a liquid crystal display (LCD), a cathode-ray tube (CRT) display, an organic electronic luminescence (EL) display, an inorganic EL display, and a plasma display, can be applied as the display 17a of the display operation interface 17. The display 17a displays a still image, a moving image, or the like of the ultrasound image data on the display screen according to the image signal output from the DSC 16 under the control of the hardware processor 18.

The touch panel 17b of the display operation interface 17 is, for example, a touch panel based on a capacitance method, which is provided so as to overlap the display panel of the display 17a. The touch panel 17b detects a contact based on a change in capacitance between the inner conductive film and the surface due to the surface being touched by the operator's fingertip or the like, and outputs a signal indicating the detected position (coordinates) to the hardware processor 18 as an operation signal. The method of the touch panel 17b is not limited to the capacitance method, and may be another method such as a resistance film method or an electromagnetic induction method.

The hardware processor 18 includes, for example, a central processing unit (CPU), a read only memory (ROM), and a random access memory (RAM), reads various processing programs such as a system program stored in the ROM and loads the processing programs to the RAM, and controls the operation of each unit of the ultrasound diagnostic apparatus 100 according to the loaded program. The ROM is a nonvolatile memory, such as a semiconductor, and stores a system program corresponding to the ultrasound diagnostic apparatus 100, various processing programs executable on the system program, various kinds of data such as a gamma table, and the like. These programs are stored in the form of computer-readable program code, and the CPU sequentially executes operations according to the program code. It is assumed that a display component registration program for executing display component registration processing, which will be described later, and an operation reception program for executing operation reception processing are stored as programs stored in the ROM. The RAM forms a work area for temporarily storing various programs executed by the CPU and data relevant to these programs.

The position detector 19 includes a digital camera, a magnetic sensor, an angular speed sensor, an acceleration sensor, and the like, and is a detector that detects the relative position of the display 17a with respect to the console 11. The position detector 19 outputs position information (display position information) of the display 17a with respect to the detected console 11 to the hardware processor 18.

The storage 20 is configured by a flash memory, a hard disk, and the like, and is a storage that stores various kinds of information, such as captured ultrasound image data, so as to be readable and writable.

For each unit included in the ultrasound diagnostic apparatus 100, some or all of the functions of the respective functional blocks can be realized as a hardware circuit such as an integrated circuit. The integrated circuit is, for example, a large scale integration (LSI), and the LSI is called an integrated circuit (IC), a system LSI, a super LSI, or an ultra LSI depending on the degree of integration. The method of circuit integration is not limited to the LSI, and may be realized by a dedicated circuit or a general-purpose processor, or a reconfigurable processor that can reconfigure the connection or setting of circuit cells inside the LSI or field programmable gate array (FPGA) may be used. Alternatively, some or all of the functions of the respective functional blocks may be executed by software. In this case, the software is stored in one or more storage media such as a ROM, an optical disk, a hard disk, or the like and the software is executed by an arithmetic processor.

Figure 3:
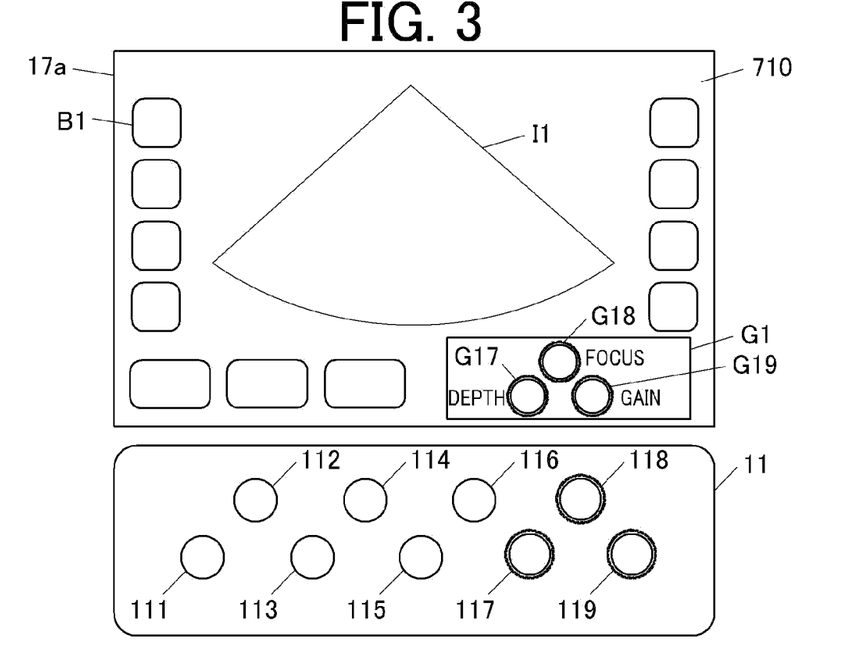
FIG. 3 is a diagram illustrating a first B-mode display screen and a console.
Figure 4:
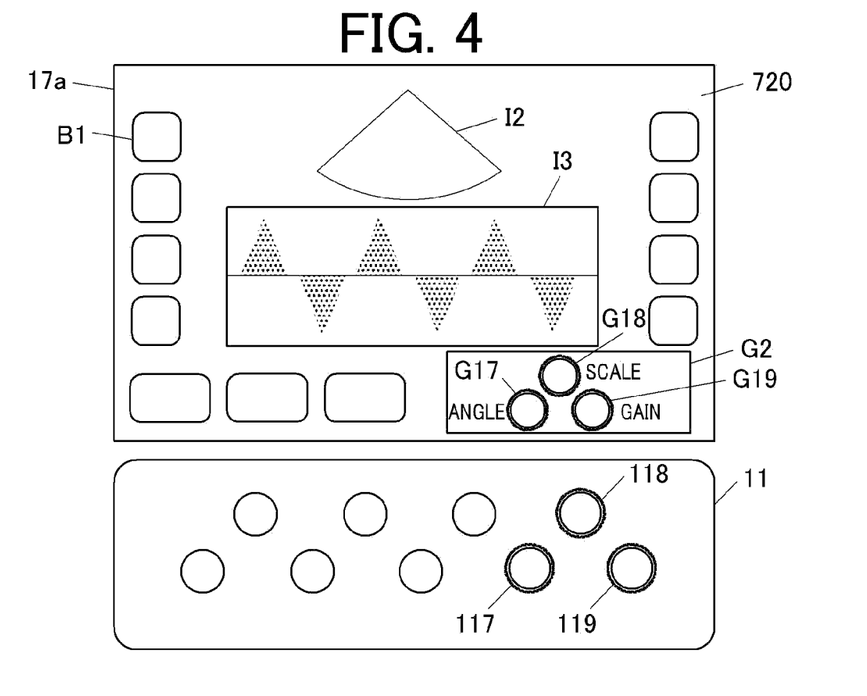
FIG. 4 is a diagram illustrating a pulse Doppler mode display screen and a console.

Next, console guide display for each image mode will be described with reference to FIGS. 3 and 4. FIG. 3 is a diagram illustrating a B-mode display screen 710 and the console 11. FIG. 4 is a diagram illustrating a pulse Doppler mode display screen 720 and the console 11.

Each physical operation device of the console 11 can set functions, which are input by operations, differently according to the image mode. Hereinafter, in order to simplify the explanation, as illustrated in FIG. 3, the console 11 will be described as an operation device having buttons 111 to 116 and rotary switches 117 to 119. However, the operation device of the console 11 is not limited to the example illustrated in FIG. 3.

As illustrated in FIG. 3, in the B-mode ultrasound image diagnosis, the display screen 710 is displayed on the display 17a. The display screen 710 includes an ultrasound image I1 and a plurality of display buttons B1 and a guide G1 for the console 11 as display components (user interface (UI) components). The ultrasound image I1 is a B-mode image. The display button B1 is a soft key that receives, for example, input of text, pictogram, and body mark, and execution input of various functions, such as measurement of an object, by touch input through the touch panel 17b. The display button B1 may be configured to receive a click input through the console 11 in a case where the console 11 includes a trackball or the like.

The guide G1 is a guide display showing functions of some frequently used operation devices (rotary switches 117 to 119) of the console 11 corresponding to the B mode. The guide G1 has display switches G17, G18, and G19 as operation display components, which correspond to the rotary switches 117, 118, and 119 in this order. In the guide G1, functions of "Depth", "Focus", and "Gain" are set in order corresponding to the display switches G17, G18, and G19, and these texts are displayed in the vicinity of each display switch. That is, the display area of the ultrasound image I1 in the depth direction can be adjusted by rotating the rotary switch 117. The focus depth of the ultrasound image I1 can be adjusted by rotating the rotary switch 118. The gain of the ultrasound image I1 can be adjusted by rotating the rotary switch 119. The position of the guide G1 on the display screen 710 (lower right end of the display screen 710) is associated with the positions (right end) of the rotary switches 117 to 119 of the console 11 so as to be close to each other. The layout (positional relationship) of the display switches G17 to G19 of the guide G1 is the same as the layout (positional relationship) of the rotary switches 117 to 119 of the console 11.

As illustrated in FIG. 4, in the pulse Doppler mode ultrasound image diagnosis, the display screen 720 is displayed on the display 17a. The display screen 720 includes ultrasound images I2 and I3 and the plurality of display buttons B1 and a guide G2 for the console 11 as display components. The ultrasound image I2 is a B-mode image, and includes a sample gate (not illustrated) in the pulse Doppler mode. The ultrasound image I3 is an image illustrating a blood flow waveform at the sample gate of the ultrasound image I2.

The guide G2 is a guide display showing functions of some frequently used operation devices (rotary switches 117 to 119) of the console 11 corresponding to the pulse Doppler mode. The guide G2 has display switches G17, G18, and G19 as operation display components, which correspond to the rotary switches 117, 118, and 119 in this order. In the guide G2, functions of "Angle", "Scale", and "Gain" are set in order corresponding to the display switches G17, G18, and G19, and these texts are displayed. That is, the angle of the sample gate of the ultrasound image I2 can be adjusted by rotating the rotary switch 117. The scale of the ultrasound image I3 can be adjusted by rotating the rotary switch 118. The gain of the ultrasound image I2 can be adjusted by rotating the rotary switch 119. The position of the guide G2 (lower right end of the display screen 720) is associated with the positions (right end) of the rotary switches 117 to 119 of the console 11 so as to be close to each other. The layout of the display switches G17 to G19 of the guide G2 is the same as the layout of the rotary switches 117 to 119 of the console 11.

As described above, functions received by a part (rotary switches 117 to 119) of the console 11 are set in advance for each image mode, and function setting information of each operation device (association between each operation device and a function) is stored for each image mode. Although the description is omitted, it is also assumed that, for the rest (buttons 111 to 116) of the console 11, the functions to be received are set in advance for each image mode, and function setting information of each operation device of the console 11 (association between each operation device and a function) for each image mode is stored in the storage 20. It is assumed that the function setting information of each operation device stored in the storage 20 can be changed according to a user input through the console 11 or the touch panel 17b.

Figure 5:
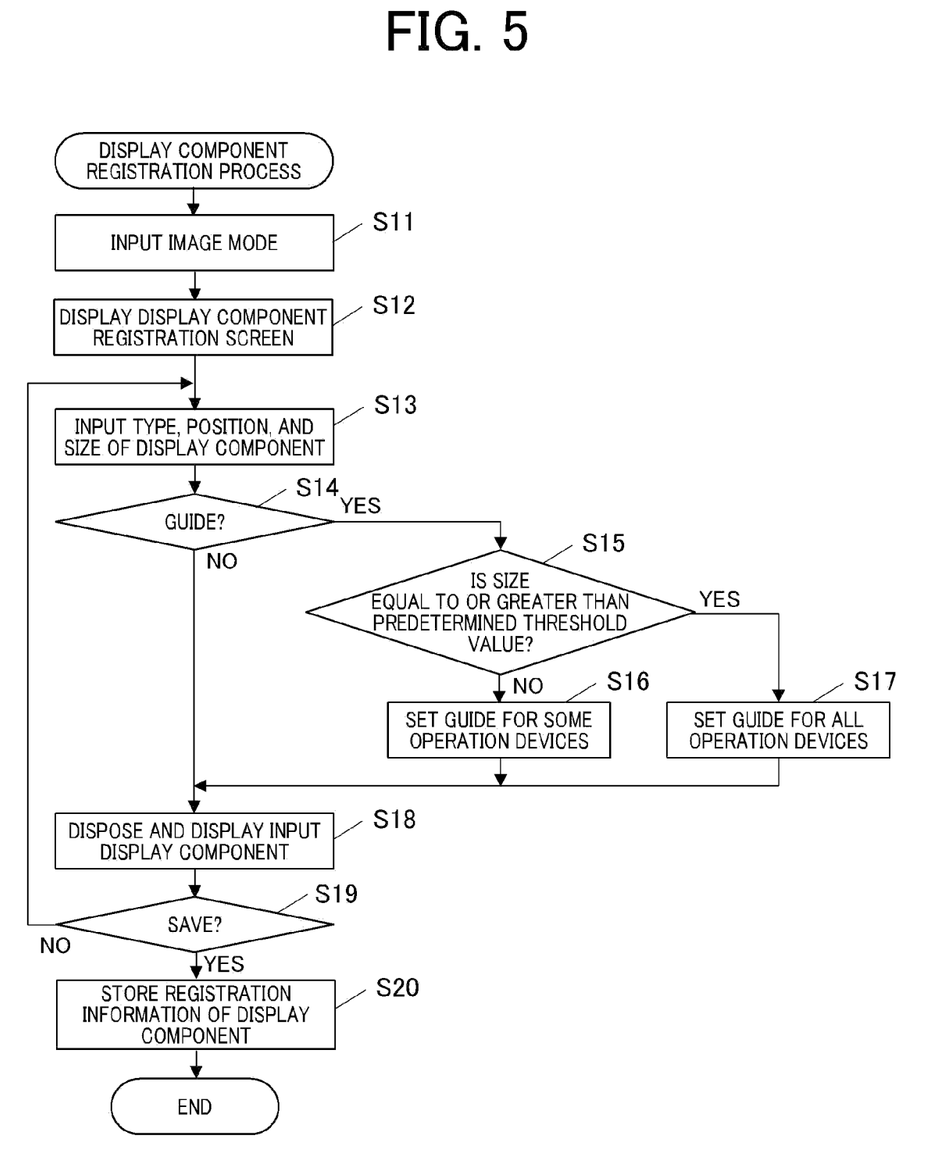
FIG. 5 is a flowchart illustrating a display component registration process.
Figure 6:
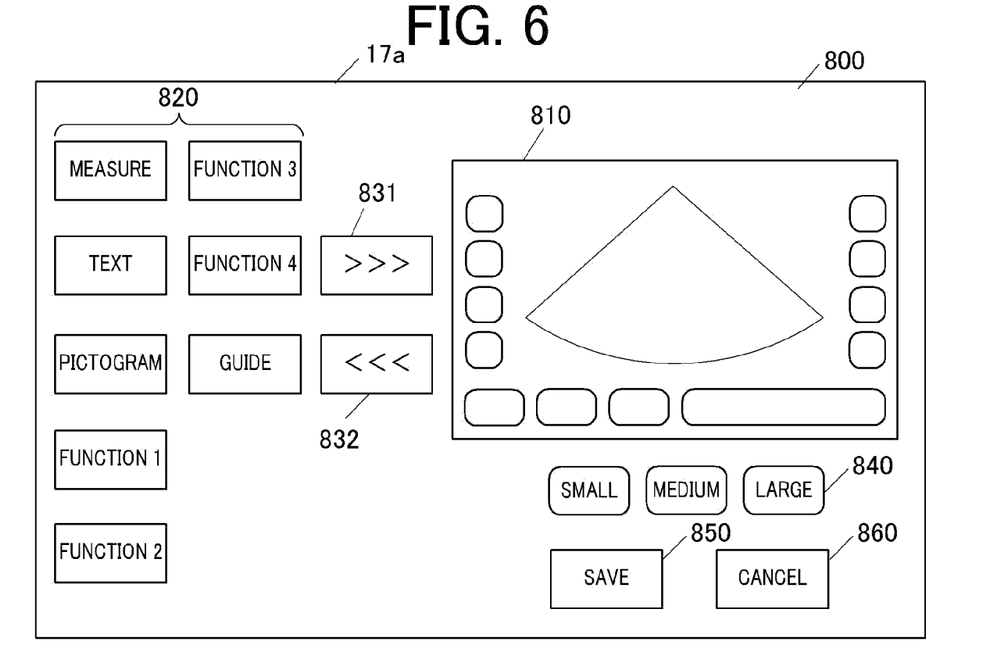
FIG. 6 is a diagram illustrating a display component registration screen.
Figure 7:
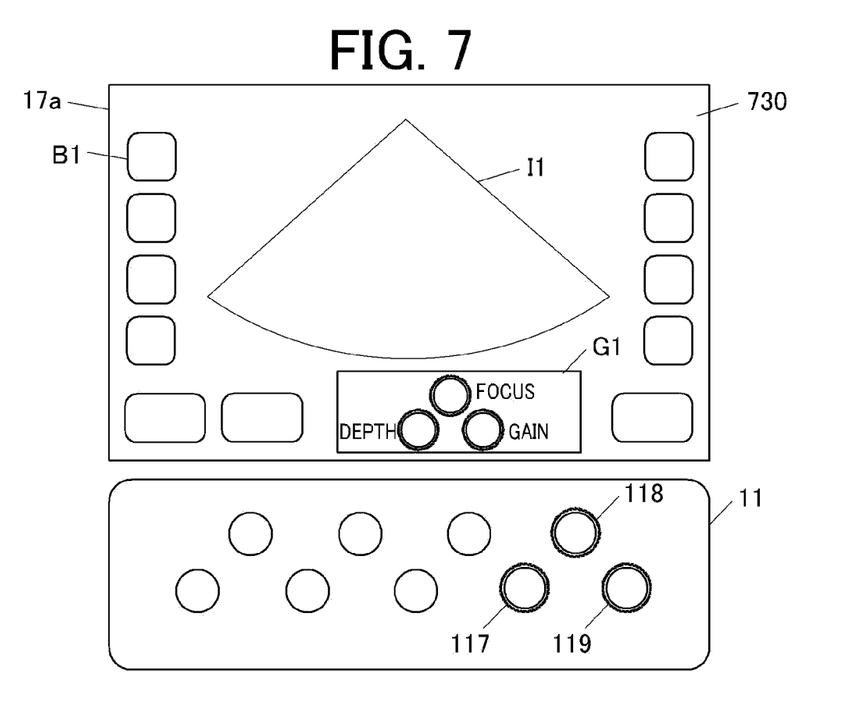
FIG. 7 is a diagram illustrating a second B-mode display screen and a console.
Figure 8:
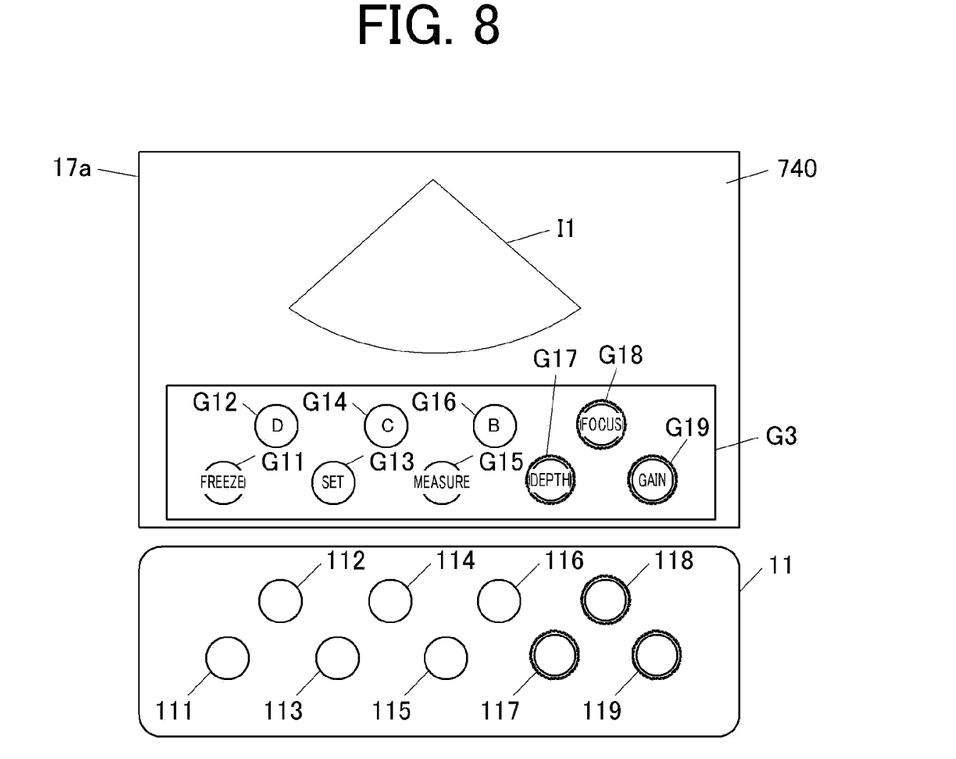
FIG. 8 is a diagram illustrating a third B-mode display screen and a console.
Figure 9:
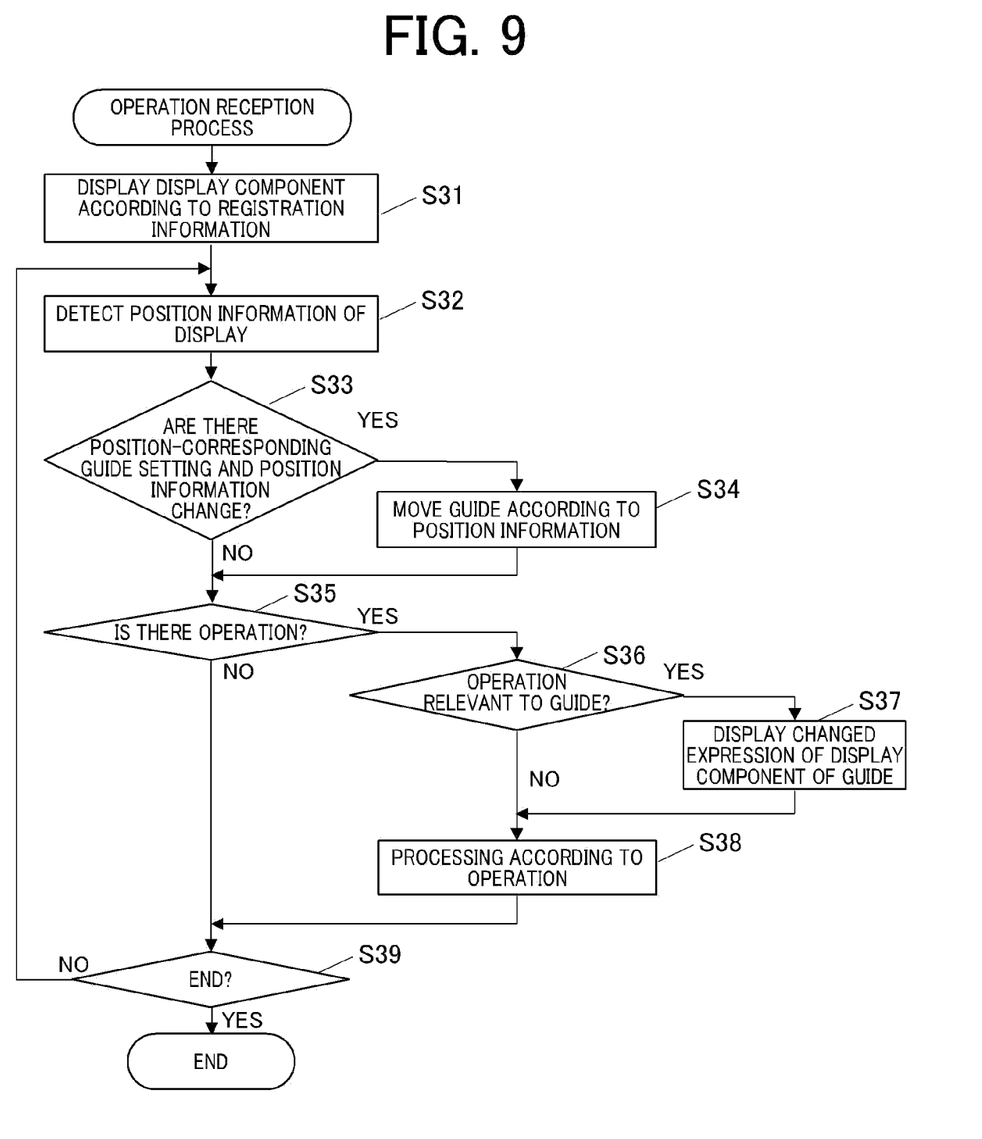
FIG. 9 is a flowchart illustrating an operation reception process.
Figure 10:
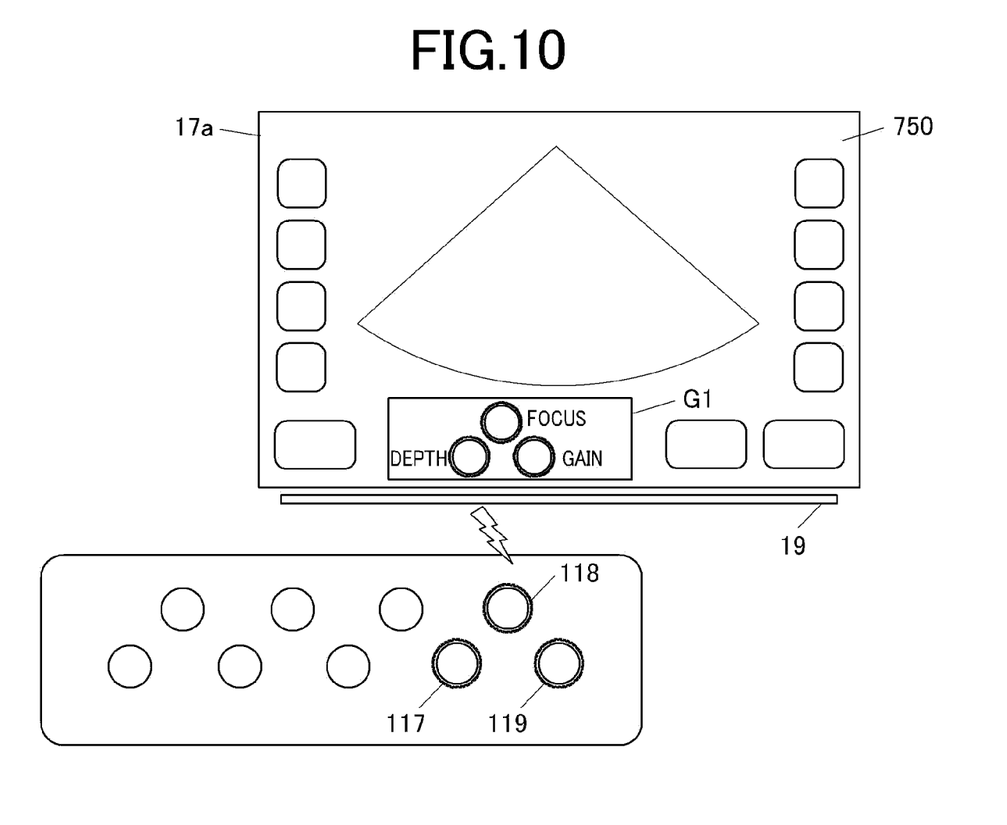
FIG. 10 is a diagram illustrating a fourth B-mode display screen and a console.
Figure 11:
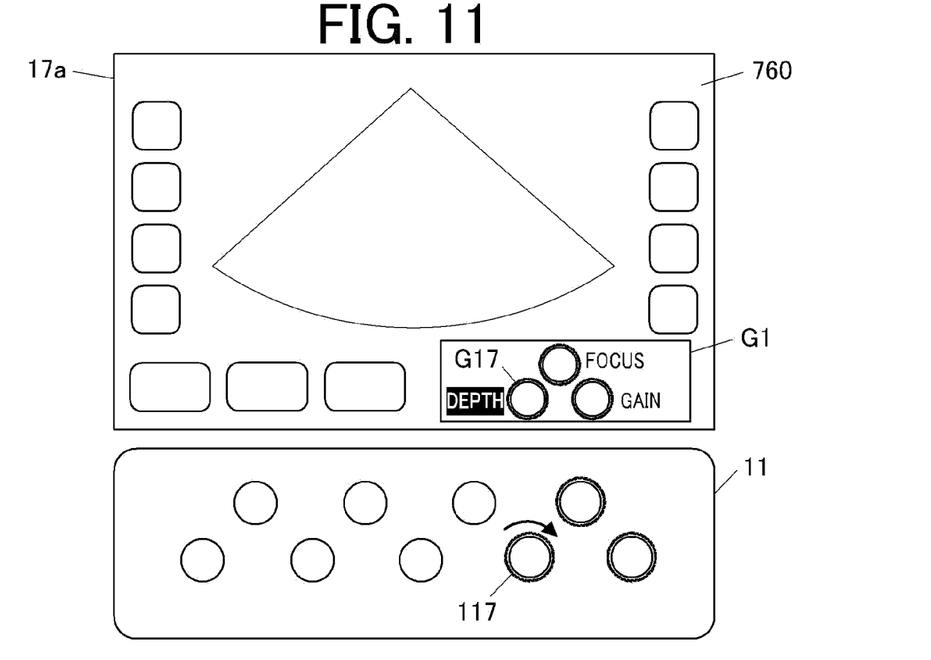
FIG. 11 is a diagram illustrating a fifth B-mode display screen and a console.
Figure 12:
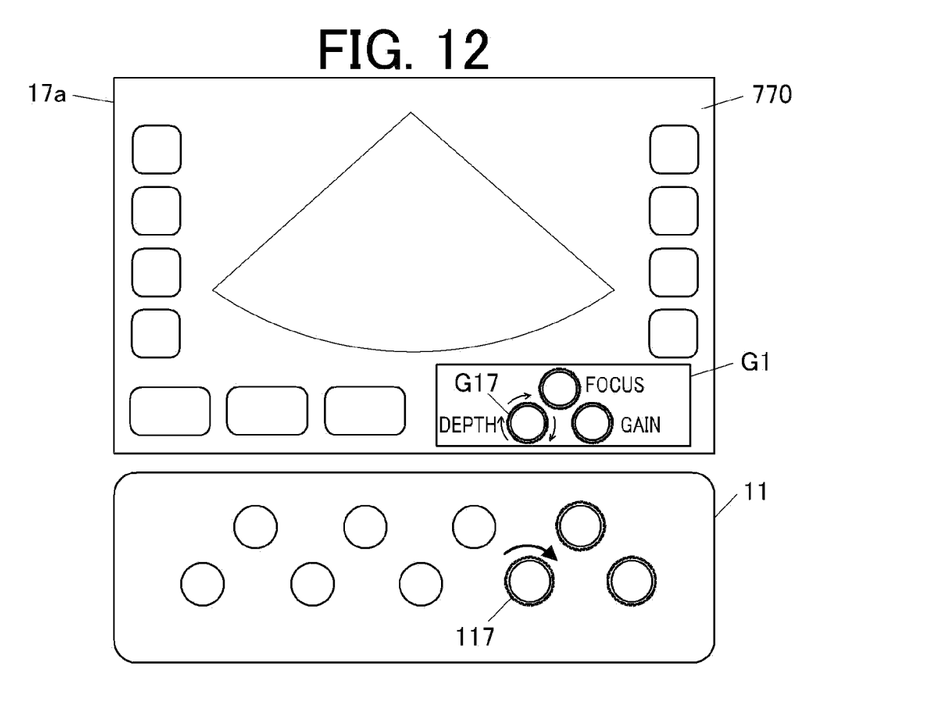
FIG. 12 is a diagram illustrating a sixth B-mode display screen and a console.

Next, the operation of the ultrasound diagnostic apparatus 100 will be described with reference to FIGS. 5 to 12. FIG. 5 is a flowchart illustrating a display component registration process. FIG. 6 is a diagram illustrating a display component registration screen 800. FIG. 7 is a diagram illustrating a B-mode display screen 730 and the console 11. FIG. 8 is a diagram illustrating a B-mode display screen 740 and the console 11. FIG. 9 is a flowchart illustrating an operation reception process. FIG. 10 is a diagram illustrating a B-mode display screen 750 and the console 11. FIG. 11 is a diagram illustrating a B-mode display screen 760 and the console 11. FIG. 12 is a diagram illustrating a B-mode display screen 770 and the console 11.

First, the display component registration process executed by the ultrasound diagnostic apparatus 100 will be described with reference to FIGS. 5 to 8. The display component registration process is a process of inputting and registering the position and size of an arbitrary type of display component as the layout of the display screen at the time of ultrasound image diagnosis in a desired image mode.

In the ultrasound diagnostic apparatus 100, for example, the hardware processor 18 executes the display component registration process according to the display component registration program stored in the ROM with an instruction to execute the display component registration process, which is input by the user such as a doctor or an engineer through the console 11 or the touch panel 17b, as a trigger.

As illustrated in FIG. 5, the hardware processor 18 receives an input of a desired image mode from the user through the console 11 or the touch panel 17b (step S11). Then, the hardware processor 18 displays display component registration screen data corresponding to the image mode input in step S11 on the display 17a (step S12). In step S12, for example, the display component registration screen 800 corresponding to the B mode illustrated in FIG. 6 is displayed.

The display component registration screen 800 includes a display screen image 810, a display component candidate button 820, an add button 831, a delete button 832, a size selection button 840, a save button 850, and a cancel button 860. The display screen image 810 is an image of a display screen in the input image mode, and also functions as an input area where display components can be disposed. The display component candidate button 820 is a button for receiving designation of a display component candidate in the input image mode. The display component candidate button 820 includes measurement, text, pictogram, functions 1 to 4, and (console 11) guide as types of display components.

The add button 831 is a display button for receiving an input to add the display component candidate designated by the display component candidate button 820 so as to be disposed on the display screen image 810. The delete button 832 is a display button for receiving an input to delete the selected display component candidate disposed on the display screen image 810. The size selection button 840 is a display button for receiving an input of the size (for example, three levels of small, medium, and large) of the selected display component candidate disposed on the display screen image 810. The save button 850 is a display button for receiving a save input with the type, position, and size of the display component disposed on the display screen image 810 as registration information. The cancel button 860 is a display button for receiving an input to cancel registration of the display component disposed on the display screen image 810.

The display component candidate button 820, the add button 831, the delete button 832, the size selection button 840, the save button 850, and the cancel button 860 can be input through the console 11 or the touch panel 17b. The display component candidate added on the display screen image 810 by the input of the add button 831 can be moved to an empty space or input for selection through the console 11 or the touch panel 17b.

Then, the hardware processor 18 receives an input of the type, position, and size of the display component from the user through the console 11 or the touch panel 17b (step S13). Incidentally, in step S13, it is assumed that the deletion input of the display component disposed on the display screen image 810 can be appropriately performed. Then, the hardware processor 18 determines whether or not the display component input in step S13 is a guide for the console 11 (step S14). When the display component input in step S13 is a guide (step S14; YES), the hardware processor 18 determines whether or not the size of the input guide is equal to or greater than a predetermined threshold value set in advance (step S15). In the present embodiment, it is assumed that whether to display a guide for all operation devices of the console 11 or display a guide for some operation devices of the console 11 is automatically selected according to whether or not the size of the guide is equal to or greater than a predetermined threshold value (for example, a value of ⅛ of the area of the display screen). For example, it is assumed that the size of the guide is equal to or greater than the predetermined threshold value when the size of the guide corresponds to "Large" of the size selection button 840 and the size of the guide is less than the predetermined threshold value when the size of the guide corresponds to "Medium" and "Small" of the size selection button 840.

When the size of the guide is less than the predetermined threshold value (step S15; NO), the hardware processor 18 sets a guide for some of the operation devices of the console 11 (step S16). When the size of the guide is equal to or greater than the predetermined threshold value (step S15; YES), the hardware processor 18 sets a guide for all the operation devices of the console 11 (step S17).

Then, the hardware processor 18 disposes and displays the display component input and set in steps S13, S16, and S17 on the display screen image 810 (step S18). Then, the hardware processor 18 determines whether or not there has been an input of the save button 850 through the console 11 or the touch panel 17b (step S19). When there is no save input (step S19; NO), the process proceeds to step S13.

When there is a save input (step S19; YES), the hardware processor 18 stores the type, position, and size of a display component and information corresponding to all or some of the operation devices of the console 11 when the display component is a guide, which are finally disposed on the display screen image 810, in the storage 20 as display component registration information in association with the image mode input in step S11 (step S20), and ends the display component registration process.

In the display component registration process, the position of the guide as a display component can be freely disposed within the empty space in step S13. For example, the guide G1 as a display component can be disposed at the lower right end of the display screen 710 so as to display the B-mode display screen 710 illustrated in FIG. 3, or the guide G1 can be disposed at the lower end of the center of the display screen 730 so as to display the B-mode display screen 730 illustrated in FIG. 7.

In the display component registration process, in steps S15 to S17, some or all of the operation display components of the operation devices included in the console 11 are appropriately set according to the size of the guide as a display component. For example, when the size of the guide is "Medium" of the size selection button 840, the guide G1 as a display component includes the display switches G17 to G19 as operation display components corresponding to some operation devices (rotary switches 117 to 119) of the console 11 so as to display the B-mode display screen 710 illustrated in FIG. 3. When the size of the guide is "Large" of the size selection button 840, the guide G3 as a display component includes display buttons G11 to G16 and the display switches G17 to G19 as operation display components corresponding to all operation devices (buttons 111 to 116 and rotary switches 117 to 119) of the console 11 so as to display the B-mode display screen 740 illustrated in FIG. 8.

Functions of "Freeze", "D (transition to pulse Doppler mode)", "Set (start point, end point, and the like of measurement)", "C (transition to color Doppler mode)", "Measure (object)", and "B (transition to B mode)" are set in order corresponding to the display buttons G11, G12, G13, G14, G15, and G16, and these texts are displayed so as to overlap the respective display buttons. On the display screen 740, the text of each function is also displayed so as to overlap each of the display switches G17 to G19. The layout of the display buttons G11 to G16 and the display switches G17 to G19 of the guide G3 is the same as the layout of the buttons 111 to 116 and the rotary switches 117 to 119 of the console 11.

Next, with reference to FIGS. 9 to 12, an operation reception process executed by the ultrasound diagnostic apparatus 100 will be described. The operation reception process is a process of receiving display component display and operation input when executing an ultrasound image display process in a desired image mode. The ultrasound image display process is a process at the time of ultrasound image diagnosis executed by the hardware processor 18, and is a process in which, according to the image mode input from the user through the console 11 or the touch panel 17b, ultrasound image data of the input image mode is generated under the control of the transmitter 12, the ultrasound probe 2, the receiver 13, and the image generator 14 and the generated ultrasound image data is displayed on the display 17a under the control of the image processor 15 and the DSC 16.

It is assumed that setting information as to whether or not to change the display position of a guide for the console 11 is input in advance corresponding to the position information of the display 17a with respect to the console 11 from the user through the console 11 or the touch panel 17b. In the ultrasound diagnostic apparatus 100, the hardware processor 18 executes the operation reception process according to the operation reception program stored in the ROM with the start of execution of the ultrasound image display process as a trigger, for example.

As illustrated in FIG. 9, first, the hardware processor 18 reads display component registration information corresponding to the image mode of the ultrasound image display process, which has been started, from the storage 20, and disposes display components including a guide on the display screen of the ultrasound image display process according to the read display component registration information and displays these on the display 17a (step S31).

Then, the hardware processor 18 detects the position information (display position information) of the display 17a with respect to the console 11 by the position detector 19 (step S32). Then, corresponding to the position information of the display 17a with respect to the console 11, the hardware processor 18 determines whether or not a setting for changing the display position of the guide for the console 11 is made and the position information of the display 17a with respect to the console 11 detected in step S32 has changed from the initial setting value or a value at the time of previous detection (step S33). When the setting for changing the display position of the guide is made and the position information of the display 17a with respect to the console 11 has changed (step S33; YES), the hardware processor 18 moves the guide for the console 11 on the display screen to a position where the corresponding operation device of the console 11 is close in accordance with the position information of the display 17a with respect to the console 11 detected in step S32 (step S34).

For example, it is assumed that, in a state in which the B-mode display screen 710 illustrated in FIG. 3 is displayed on the display 17a and the guide G1 is disposed at the lower right end of the display screen, the display 17a is moved rightward by the user through the arm 17c as illustrated in FIG. 10. Then, the display screen 750, which is obtained after the position information of the display 17a with respect to the console 11 is detected in step S32 and the guide G1 is disposed at the lower left end of the center of the display screen so that the guide G1 is close to the rotary switches 117 to 119 corresponding to the position information of the display 17a with respect to the console 11 in step S34, is displayed on the display 17a.

After executing step S34, or when the setting for changing the display position of the guide is not made, or when the setting for changing the display position of the guide is made and the position information of the display 17a with respect to the console 11 has not changed (step S33; NO), the hardware processor 18 determines whether or not there is an operation input from the user through the console 11 or the touch panel 17b (step S35).

When there is an operation input (step S35; YES), the hardware processor 18 determines whether or not the operation input in step S35 is an operation relevant to the guide for the console 11 (step S36). The operation relevant to the guide is a direct touch operation on operation display components (display buttons G11 to G16 and display switches G17 to G19) included in the guide, or an operation on operation devices (buttons 111 to 116 and rotary switches 117 to 119) of the console 11 corresponding to the display components included in the guide.

When the operation input in step S35 is an operation relevant to the guide for the console 11 (step S36; YES), the hardware processor 18 changes the expression of the operation display components (display buttons G11 to G16 and display switches G17 to G19) of the guide to an expression indicating "in operation" and displays these (step S37). One of the expressions indicating "in operation" in step S37 is a text highlight display of the function of each display component. For example, when the rotary switch 117 of the console 11 is rotated by the user while the B-mode display screen 710 is displayed on the display 17a as illustrated in FIG. 3, in step S37, the display screen 760 under inverted display is displayed on the display 17a so that the text of "depth" corresponding to the display switch G17 is highlighted as illustrated in FIG. 11. Highlight display is not limited to the inverted display, and may be character color conversion, character blinking, character background color conversion, character size conversion, and the like. When the display buttons G11 to G16 are included in the guide and the buttons 111 to 116 are pressed, the text of the display buttons corresponding to the pressing is highlighted.

One of the expressions indicating "in operation" in step S37 is a moving image expression indicating the movement of a display component operation. For example, when the rotary switch 117 of the console 11 is rotated clockwise by the user while the B-mode display screen 710 is displayed on the display 17a as illustrated in FIG. 3, in step S37, the display screen 760 displayed as a moving image (expressed by three arrows in the diagram) in which the display switch G17 rotates clockwise is displayed on the display 17a as illustrated in FIG. 12.

After executing step S37 or when the operation input in step S35 is not an operation relevant to the guide for the console 11 (step S36; NO), the hardware processor 18 performs processing on the operation input in step S35 (step S38). Step S38 includes processing similar to that in step S31 in the changed image mode in a case where there is an operation input for changing the image mode. Then, the hardware processor 18 determines whether or not to end the operation reception process in accordance with the end of the ultrasound image display process being executed (step S39). When the operation reception process is not ended (step S39; NO), the process proceeds to step S32. When the operation reception process is ended (step S39; YES), the operation reception process ends.

As described above, according to the present embodiment, the ultrasound diagnostic apparatus 100 includes the image generator 14 that generates ultrasound image data based on the reception signal obtained through the ultrasound probe 2, the display 17a, the hardware processor 18 that displays the generated ultrasound image data on the display 17a, and the console 11 having a plurality of physical operation devices (buttons 111 to 116 and rotary switches 117 to 119) for receiving an operation input. The hardware processor 18 registers display position information, which is information regarding the display position within the display screen of the guide including operation display components (for example, display switches G17 to G19) corresponding to the operation devices of the console 11 and information indicating the functions set for the operation devices, in the storage 20 and displays the guide on the display 17a based on the display position information stored in the storage 20.

Therefore, since the position of the guide can be arbitrarily set and registered, the guide can be disposed at a position that does not overlap an ultrasound image within the display screen. As a result, since the user can visually check the function of the operation device corresponding to each operation display component of the guide without interfering with the ultrasound image diagnosis, the corresponding operation device of the console 11 can be easily operated.

The guide includes a plurality of operation display components corresponding to the plurality of operation devices. Therefore, since the user can visually check the association between the plurality of operation devices and the plurality of operation display components, the corresponding operation device of the console 11 can be easily operated.

The layout of the plurality of operation display components of the guide corresponds to the layout of the plurality of operation devices of the console 11. Therefore, since the user can visually check the association between the plurality of operation devices and the plurality of operation display components more easily, the corresponding operation device of the console 11 can be more easily operated.

The hardware processor 18 sets the display content of the guide according to the size of the guide, and registers display position information within the display screen of the guide, for which the display content is set, in the storage 20. Specifically, the hardware processor 18 determines whether or not the size of the guide is equal to or greater than a predetermined threshold value, and sets the guide as a guide having operation display components corresponding to all the operation devices of the console 11 when the size of the guide is equal to or greater than the predetermined threshold value. Therefore, when the guide is large, the functions of all the operation devices of the console 11 can be visually recognized.

When the size of the guide is less than the predetermined threshold value, the hardware processor 18 sets the guide as a guide having operation display components corresponding to some operation devices of the console 11. Therefore, when the guide is small, the functions of some more important operation devices of the console 11 can be visually recognized.

The ultrasound diagnostic apparatus 100 also includes the position detector 19 that detects the position of the display 17*a* and outputs display position information. The hardware processor 18 sets the position of the guide within the display screen according to the display position information. Specifically, the hardware processor 18 sets the position of the guide within the display screen to a position close to the corresponding portion of the console 11 according to the detected position information of the display 17*a*. Therefore, the corresponding portion of the console 11 and the guide are easily associated, so that the guide can be visually recognized.

The hardware processor 18 changes the expression of the operation display component of the guide corresponding to the operation device being operated. More specifically, the hardware processor 18 displays a similar operation of the operation display component of the guide corresponding to the operation of the operation device being operated. Therefore, the function of the operation display component of the guide corresponding to the operation device, which is being operated, of the console 11 can be checked more easily.

The hardware processor 18 highlights the function of the operation display component of the guide corresponding to the operation device being operated. Therefore, the function of the operation display component of the guide corresponding to the operation device, which is being operated, of the console 11 can be checked more easily.

The hardware processor 18 receives a touch operation input to the operation display component of the guide corresponding to the operation input to the operation device through the touch panel 17*b*. Therefore, the operation input can be performed more easily by a direct operation on the operation device of the console 11 and a touch operation on the operation display component of the guide.

In the above description, an example in which the ROM is used as a computer-readable medium of the program according to the present invention is disclosed. However, the invention is not limited to this example. As other computer-readable media, a non-volatile memory, such as a flash memory, and a portable recording medium, such as a CD-ROM, can be applied. A carrier wave is also applied to the present invention as a medium for providing data of the program according to the present invention through a communication line.

The description in the above embodiment is examples of preferable ultrasound diagnostic apparatus, recording medium, and console guide display method according to the present invention, but the invention is not limited thereto.

In the above embodiment, the ultrasound diagnostic apparatus 100 has been described in which the display 17*a* and the console 11 are separated from each other and the display 17*a* and the ultrasound diagnostic apparatus body 1 are connected to each other by the arm 17*c*. However, the invention is not limited to this configuration. For example, the ultrasound diagnostic apparatus body 1 may be configured not to include the arm 17*c*. The configuration for guide registration and display in the above embodiment may be applied to an ultrasound diagnostic apparatus in which a display and a console are integrally connected. In the ultrasound diagnostic apparatus in which the display and the console are integrally connected, the display may be configured to be movable with respect to the console by rotation or the like. Also in this configuration, the guide within the display screen may be appropriately moved and displayed so that the guide within the display screen of the display and a portion of the console corresponding to the guide are close to each other.

Although embodiments of the present invention have been described and illustrated in detail, the disclosed embodiments are made for purposes of illustration and example only and not limitation. The scope of the present invention should be interpreted by terms of the appended claims.

The detailed configuration and detailed operation of each unit configuring the ultrasound diagnostic apparatus 100 in the above embodiment can be appropriately changed without departing from the spirit of the present invention.

What is claimed is:

1. An ultrasound diagnostic apparatus, comprising:
   a first hardware processor that generates ultrasound image data based on a reception signal obtained through an ultrasound probe;
   a display;
   a second hardware processor that causes the display to display the generated ultrasound image data;
   a console that has a plurality of physical operation devices that receive an operation input, the physical operation devices are hardware input devices located at fixed locations on the console,
   wherein the second hardware processor stores display position information, which is information regarding a display position within a display screen of a guide including operation display components corresponding to respective operation devices of the plurality of physical operation devices of the console and information indicating a function of the respective operation devices, in a storage and displays the guide on the display based on the display position information stored in the storage, the positional relationship of the operation display components of the guide is the same as the positional relationship of the respective operation devices of the console; and
   a position detector that detects a position of the display, the position of the display being adjustable relative to the console, wherein the second hardware processor sets the guide within the display screen to a position proximate the respective operation devices of the console based on the position of the display relative to the console.

2. The ultrasound diagnostic apparatus according to claim 1,
wherein the second hardware processor sets a display content of the guide according to a size of the guide, and registers display position information within the display screen of the guide, for which the display content is set, in the storage.

3. The ultrasound diagnostic apparatus according to claim 2,
wherein the second hardware processor determines whether or not a size of the guide is equal to or greater than a predetermined threshold area value, and sets the guide as a guide having operation display components corresponding to all of the plurality of physical operation devices of the console when the size of the guide is equal to or greater than the predetermined threshold area value.

4. The ultrasound diagnostic apparatus according to claim 3,
wherein the second hardware processor sets the guide as a guide having operation display components corresponding to some of the plurality of physical operation devices of the console when the size of the guide is less than the predetermined threshold area value.

5. The ultrasound diagnostic apparatus according to claim 1,
wherein the second hardware processor sets the position of the guide within the display screen to a position close to the respective operation devices of the console.

6. The ultrasound diagnostic apparatus according to claim 1,
wherein the second hardware processor changes the expression of the one of the plurality of operation components by displaying a moving image expression indicating a movement of the operation of the one of the plurality of physical operation devices.

7. The ultrasound diagnostic apparatus according to claim 1,
wherein the second hardware processor changes the expression of the one of the plurality of operation components to highlight a function of the one of the plurality of physical operation devices.

8. The ultrasound diagnostic apparatus according to claim 1,
wherein the second hardware processor receives a touch operation input to the operation display component corresponding to an operation input to the operation device through a touch panel provided in the display.

9. A non-transitory recording medium storing a computer readable program causing a computer to function as:
a first hardware processor that generates ultrasound image data based on a reception signal obtained through an ultrasound probe;
a display;
a second hardware processor that causes the display to display the generated ultrasound image data;
wherein the second hardware processor stores display position information, which is information regarding a display position within a display screen of a guide including operation display components corresponding to respective operation devices of a plurality of physical operation devices of a console, the physical operation devices being hardware input devices located at fixed locations on the console that receive an operation input, and information indicating a function of the respective operation devices, in a storage and displays the guide on the display based on the display position information stored in the storage, the positional relationship of the operation display components of the guide is the same as the positional relationship of the respective operation devices of the console; and
wherein the computer is made to function as a position detector that detects a position of the display relative to the console and outputs display position information, and
the second hardware processor sets a position of the guide within the display screen according to the display position information.

10. The non-transitory recording medium storing a computer readable program according to claim 9,
wherein the second hardware processor sets a display content of the guide according to a size of the guide, and registers display position information within the display screen of the guide, for which the display content is set, in the storage.

11. The non-transitory recording medium storing a computer readable program according to claim 10,
wherein the second hardware processor determines whether or not a size of the guide is equal to or greater than a predetermined threshold area value, and sets the guide as a guide having operation display components corresponding to all of the plurality of physical operation devices of the console when the size of the guide is equal to or greater than the predetermined threshold area value, and sets the guide as a guide having operation display components corresponding to some of the plurality of physical operation devices of the console when the size of the guide is less than the predetermined threshold area value.

12. The non-transitory recording medium storing a computer readable program according to claim 9,
wherein the second hardware processor receives a touch operation input to the operation display component corresponding to an operation input to the operation device through a touch panel provided in the display.

13. A console guide display method, comprising:
generating ultrasound image data based on a reception signal obtained through an ultrasound probe;
performing display control to display the generated ultrasound image data on a display; and
storing display position information, which is information regarding a display position within a display screen of a guide including operation display components corresponding to respective operation devices of a plurality of physical operation devices of a console, the plurality of physical operation devices being hardware input devices located at fixed locations on the console that are capable of receiving an operation input, and information indicating a function of the operation device, in a storage, the positional relationship of the operation display components of the guide is the same as the positional relationship of the respective operation devices of the console,
wherein, in the display control, the guide is displayed on the display based on the display position information stored in the storage;
detecting a position of the display, which is adjustable relative to the console; and setting the guide within the display screen to a position proximate the respective operation devices of the console based on the position of the display relative to the console.

14. The ultrasound diagnostic apparatus according to claim 1,
wherein the information indicating a function on the guide provides an indication associating a specific function with each of the respective operation devices on the console.

15. The non-transitory recording medium storing a computer readable program according to claim 9,
wherein the information indicating a function on the guide provides an indication associating a specific function with each of the respective operation devices on the console.

16. The ultrasound diagnostic apparatus according to claim 1, wherein the second hardware processor changes the position of the guide within the display screen in response to a change in the position of the display relative to the console.

17. The ultrasound diagnostic apparatus according to claim 1, wherein the second hardware processor changes an expression of one of the operation display components of the guide when a corresponding one of the plurality of physical operation devices of the console is being operated to indicate that the one of the plurality of physical operation devices is in operation.

* * * * *